United States Patent [19]

Cady et al.

[11] Patent Number: 5,069,370

[45] Date of Patent: Dec. 3, 1991

[54] LARGE SCALE LIQUID MEDIA DISPENSING AND SUPPLEMENTING SYSTEM

[75] Inventors: David J. Cady, Snyder; Kevin R. Hall, Grand Island, both of N.Y.; Robert W. Lynn, Silver Spring, Md.

[73] Assignee: Life Technologies, Inc., Gaithersburg, Md.

[21] Appl. No.: 564,360

[22] Filed: Aug. 8, 1990

Related U.S. Application Data

[63] Continuation-in-part of Ser. No. 541,908, Jun. 22, 1990.

[51] Int. Cl.⁵ .............................................. B67D 5/60
[52] U.S. Cl. .................................. 222/464; 222/318; 222/481.5; 55/385.4; 366/137
[58] Field of Search ................... 55/385.4, 505; 251/7; 366/136, 137, 140; 222/189, 145, 318, 464, 481.5, 482; 73/363.85, 364.73, 364.91; 220/85 SP; 378/66

[56] References Cited

U.S. PATENT DOCUMENTS

| | | | |
|---|---|---|---|
| 1,728,771 | 9/1929 | Shaw | 222/318 |
| 2,542,855 | 2/1951 | Willison | 222/145 |
| 3,185,348 | 5/1965 | Pollak et al. | 222/146.6 |
| 4,056,981 | 11/1977 | Kalka et al. | 73/863.85 |
| 4,386,637 | 6/1983 | Buchanan et al. | 222/49 |
| 4,457,758 | 7/1984 | Norton | 73/863.85 |
| 4,522,789 | 6/1985 | Kelly et al. | 222/109 |
| 4,548,344 | 10/1985 | Hestehave et al. | 222/464 |
| 4,750,643 | 6/1988 | Wortrich | 222/482 |
| 4,796,677 | 1/1989 | Nice | 222/109 |

FOREIGN PATENT DOCUMENTS

| | | | |
|---|---|---|---|
| 0354665 | 2/1990 | European Pat. Off. | 222/318 |
| 428848 | 5/1926 | Fed. Rep. of Germany | 222/482 |
| 3717823 | 12/1987 | Fed. Rep. of Germany | 73/864.73 |
| 735659 | 8/1955 | United Kingdom | 222/464 |

*Primary Examiner*—Kevin P. Shaver
*Assistant Examiner*—Kenneth Bomberg
*Attorney, Agent, or Firm*—Sterne, Kessler, Goldstein & Fox

[57] ABSTRACT

Disclosed is a system for dispensing and supplementing a large volume of liquid for use with cell and tissue cultures. The system disclosed comprises a large volume drum having liquid contained therein. The system disclosed further comprises a first assembly for dispensing the liquid from the large volume drum. The system disclosed further comprises a second assembly for supplementing the first liquid contained in the large volume drum with the second liquid. The system disclosed may also comprise a third mechanical arrangement for mixing the first and second liquids. The materials chosen are compatible with gamma irradiation sterilization process, sterile cell culture media, and standard distribution systems.

11 Claims, 6 Drawing Sheets

LARGE SCALE LIQUID MEDIA DISPENSING AND SUPPLEMENTING SYSTEM

RELATED APPLICATIONS

This application is a continuation-in-part of U.S. application Ser. No. 07/541,908, filed Jun. 22, 1990.

BACKGROUND OF THE INVENTION

1. Field of the Invention

The present invention relates generally to liquid dispensing systems. More particularly, the present invention relates to a dispensing and supplementation system for large volumes of various liquids for use with cell and tissue cultures.

2. Related Art

Scientists and technicians working in the biotechnology sciences often require the use of liquid media for use with cell and tissue cultures. To obtain the most cost effective and efficient results with cell and tissue culture, it is often desirable to use large volumes of liquid media for a given experiment or process.

One such system is manufactured by JRH Bio-Sciences, Inc. This system consists of a well bucket having a plastic bag mounted therein. The plastic bag has one port with one associated fluid line attached thereto. The liquid media contained within the bag can only be dispensed.

Another type of liquid dispensing system is that referred to as a "STAK PACK" design. The STAK PACK system comprises a plurality of individual liquid containers that can be serially attached to create a large multiple unit fluid system. The liquid media can be dispensed via a dispensing port and filled via a filling port.

Conventional systems of the type described above have several disadvantages. First, conventional systems can typically only provide small volumes of liquid media. Small volume liquid media systems become present significant problems when attempting to prepare or diagnose certain types of cell and tissue cultures.

Second, conventional systems can only dispense the liquid media and do not offer the user the ability to supplement the liquid media. In diagnostic testing and preparation, it is often advantageous to modify the working liquid media fluid so that variations can be experimented with. The ability to supplement as opposed to preparing a new solution is a significant advantage to people working in the biotechnology industry.

Third, conventional systems typically have only one dispensing port. In systems of this type, the user must adapt their internal distribution systems to that of the dispensing systems. This is a significant disadvantage.

SUMMARY OF THE INVENTION

The system of the present invention is particularly adapted to handle large volumes of various sterile liquids for use with cell and tissue cultures. The system of the present invention generally comprises a large volume drum containing a first liquid, means for dispensing the first liquid from the large volume drum, and means for supplementing the first liquid contained in the large volume drum with a second liquid. Further provided in the system of the present invention is means for uniformly mixing the first and second liquids.

The dispensing means generally comprises a dispensing cap attached to the large volume drum. The dispensing cap comprises an internal dispensing port and an external dispensing port. The internal dispensing port and the external dispensing port are in communication with each other. The dispensing cap further comprises an internal sampling port and an external sampling port. The internal sampling port and the external sampling port are in communication with each other.

The dispensing means further comprises an internal dispensing line connected to the internal dispensing port and an external dispensing line connected to the external dispensing port. The internal dispensing line and the external dispensing line carry the liquid from the drum to the external source. Additionally, the external and internal dispensing line provides a means to initially fill the drum.

The dispensing means further comprises an internal sampling line connected to the internal sampling port and an external sampling line connected to the external sampling port. The internal sampling line and the external sampling line are provided such that the end user may sample small volumes of the liquid contained in the drum.

The supplementing means generally comprises a supplementation cap that is attached to the drum. The supplementation cap generally comprises an internal supplementation port and external supplementation port. The internal and external supplementation ports provide communication between the inside of the drum and the external environment.

The supplementing means further comprises an internal supplementation line connected to the internal supplementation port and an external supplementation line connected to the external supplementation port. The internal supplementation line and the external supplementation line provide the mechanism that carries the supplement liquid into the drum from the external source.

The mixing means generally comprises the dispensing means and supplementation means heretofore described. In the mixing mode, the external dispensing line is connected with the external supplementation line. Thereafter conventional pumping apparatus is applied to the system to generate a fluid circulation from the bottom of the drum to the top of the drum. This circulation results in the supplement liquid being mixed with the original liquid.

Each of the components that come in contact for a substantial duration of time with the sterile supplement or sterile primary liquid are pre-sterilized. Pre-sterilization ensures that the sterile liquid(s) are not contaminated. The sterilization process is performed using gamma irradiation protocols. The chosen materials are compatible with such a sterilizing technique.

BRIEF DESCRIPTION OF THE DRAWINGS

Various objects, features and attendant advantages of the present invention will be more fully understood from the following detailed description of the present invention when considered in connection with the accompanying drawings, in which.

DETAILED DESCRIPTION OF THE PREFERRED EMBODIMENTS

The present invention is an integrated aseptic supplementation, mixing, and dispensing system and method. The system and method of the present invention allows for the sterile supplementation, mixing and dispensing of large volumes of various sterile liquids for cell and tissue cultures. As will be more fully understood from the following detailed description, the present invention has the ability to supplement, mix and dispense through normal distribution environments and is manufactured using conventional components. The system of the present invention can provide scientists and technicians economical large scale volumes of various sterile liquids heretofore unavailable in conventional dispensing systems.

Figure 1:
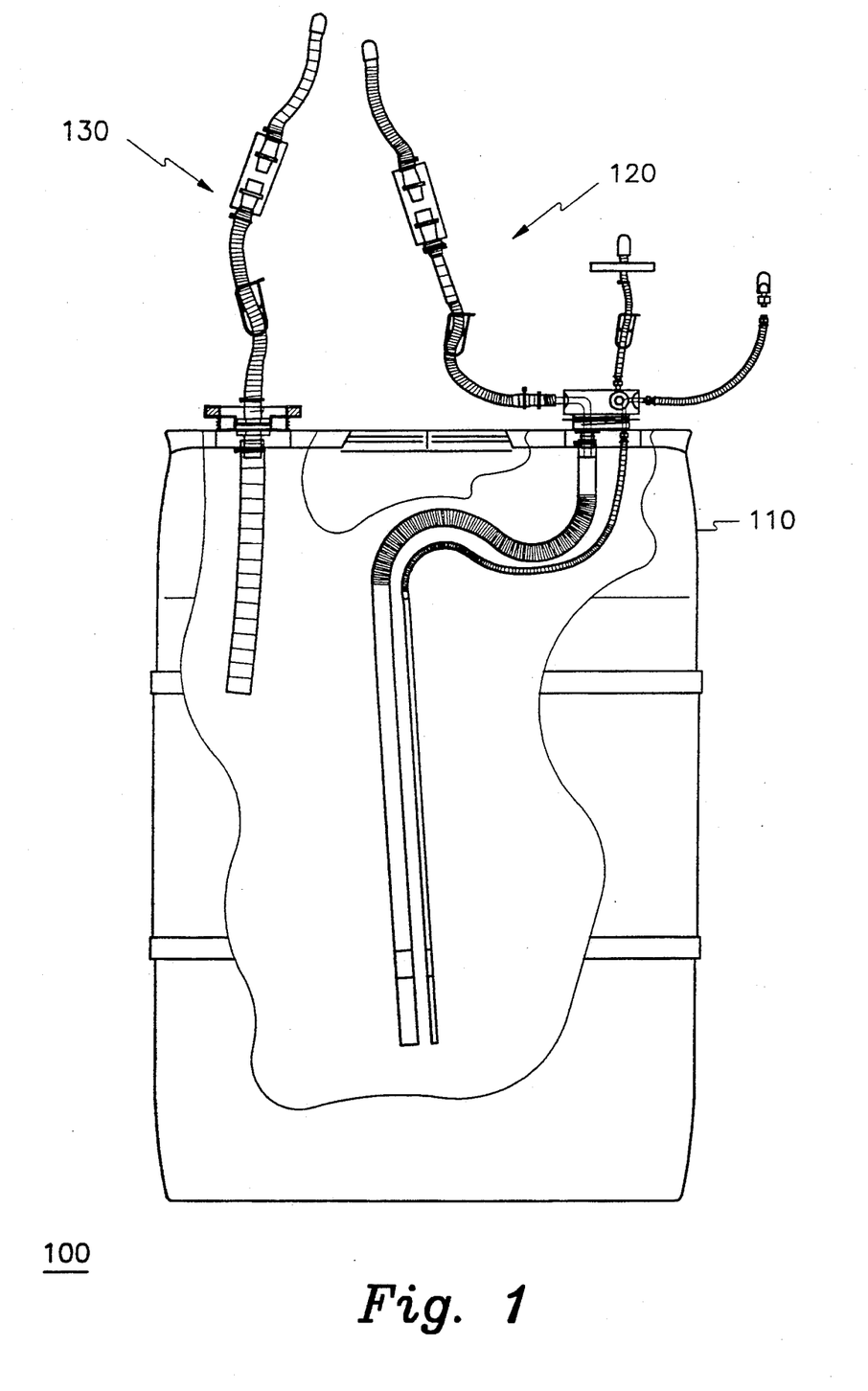
FIG. 1 is a partial cut-away, perspective view of the preferred embodiment of the present invention.

Referring first to FIG. 1, the system of the present invention comprises a drum 110, a dispensing assembly 120, and a supplementation assembly 130. Drum 110, as will be more fully described herein, is generally provided to aseptically contain large scale volumes of various liquids for cell and tissue cultures.

Dispensing assembly 120, as will be more fully described herein, generally functions to aseptically dispense the liquid contained within drum 110 to an external point. Such external point may be that of a cell growth or testing apparatus. Dispensing assembly 120 is designed to offer several ways of aseptically dispensing the liquid contained in drum 110. In one dispensing mode, dispensing assembly 120 provides high volume dispensing. In another dispensing mode, dispensing assembly 120 provides low volume dispensing or low volume supplementation. Low volume dispensing, for example, may be required when the liquid media in drum 110 need only be sampled or dispensed very slowly.

Supplementation assembly 130, as will be more fully described herein, generally functions to supplement (add) a secondary liquid to a primary liquid contained in drum 110. Supplementation assembly 130 allows the user to add a variety of sterile liquids to the original sterile liquid contained in drum 110. The ability to supplement large scale volumes of the original sterile liquid contained in drum 110 is a significant advantage in diagnostic testing and batch processing.

As will be described in more detail herein, the present invention also provides a mixing feature. The mixing feature generally allows the supplement added via the supplementation assembly 130 to be uniformly mixed with the original liquid. This feature is generally achieved by connecting the dispensing assembly 120 to the supplementation assembly 130.

Figure 2:
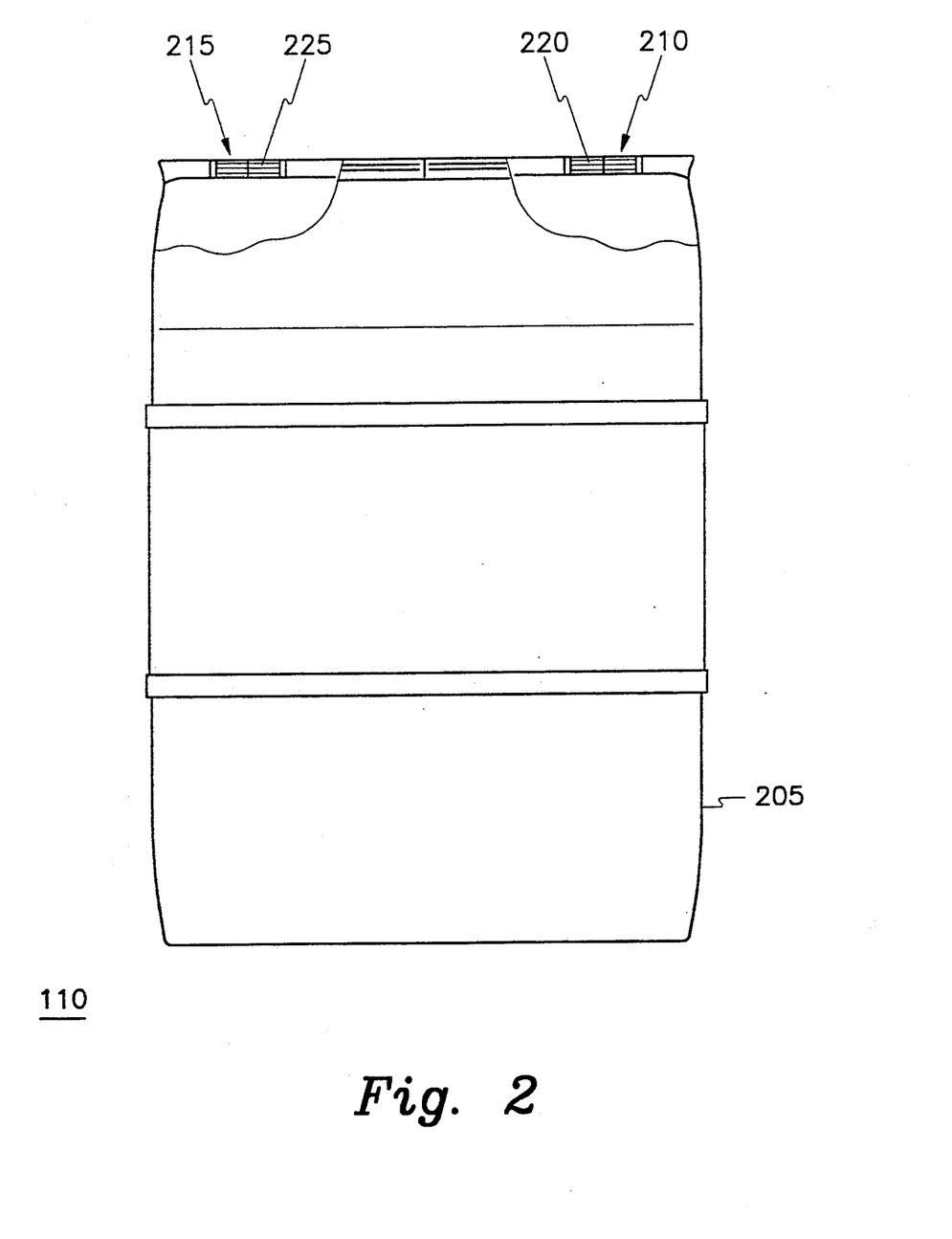
FIG. 2 is a detailed view of the drum.

Referring next to FIG. 2, drum 110 generally comprises a body 205, a dispensing port 210 and a supplementation port 215. Dispensing port 210 is provided so that the dispensing assembly 120 may be securely and sealably attached thereto. Dispensing port 210 is sometimes referred to as a bung hole. In the preferred embodiment, dispensing port 210 is formed as part of body 205 and has buttress grooves 220.

Supplementation port 215 is provided so that supplementation assembly 130 may be securely and sealably attached thereto. Supplementation port 215 has standard National pipe thread (NPT) grooves 225. Like dispensing port 210, supplementation port 215 is formed as a part of body 205.

Drum 110 of the preferred embodiment is made from high density polyethelene (HDPE). High density polyethelene is the preferred material when the system of the present invention is to be used with sterile liquids because it is compatible with a gamma irradiation process. The gamma irradiation process is the preferred technique used to sterilize the drum, and other components of the present invention (to be described). The gamma irradiation process is well known in the art. Drum 110, however, can be other materials such as polypropulene, polycarbonate or non-plastics such as metal. Materials such as polypropulene or polycarbonate, however, may not be as compatible as high density polyethelene is with the gamma irradiation process.

Drum 110 of the preferred embodiment has a 55-gallon volume capacity. Drum 110, however, may be designed to contain a smaller or larger volume of liquid. Drum 110 may also be designed to contain liquids other than those used for cell and tissue culture applications.

Figure 3:
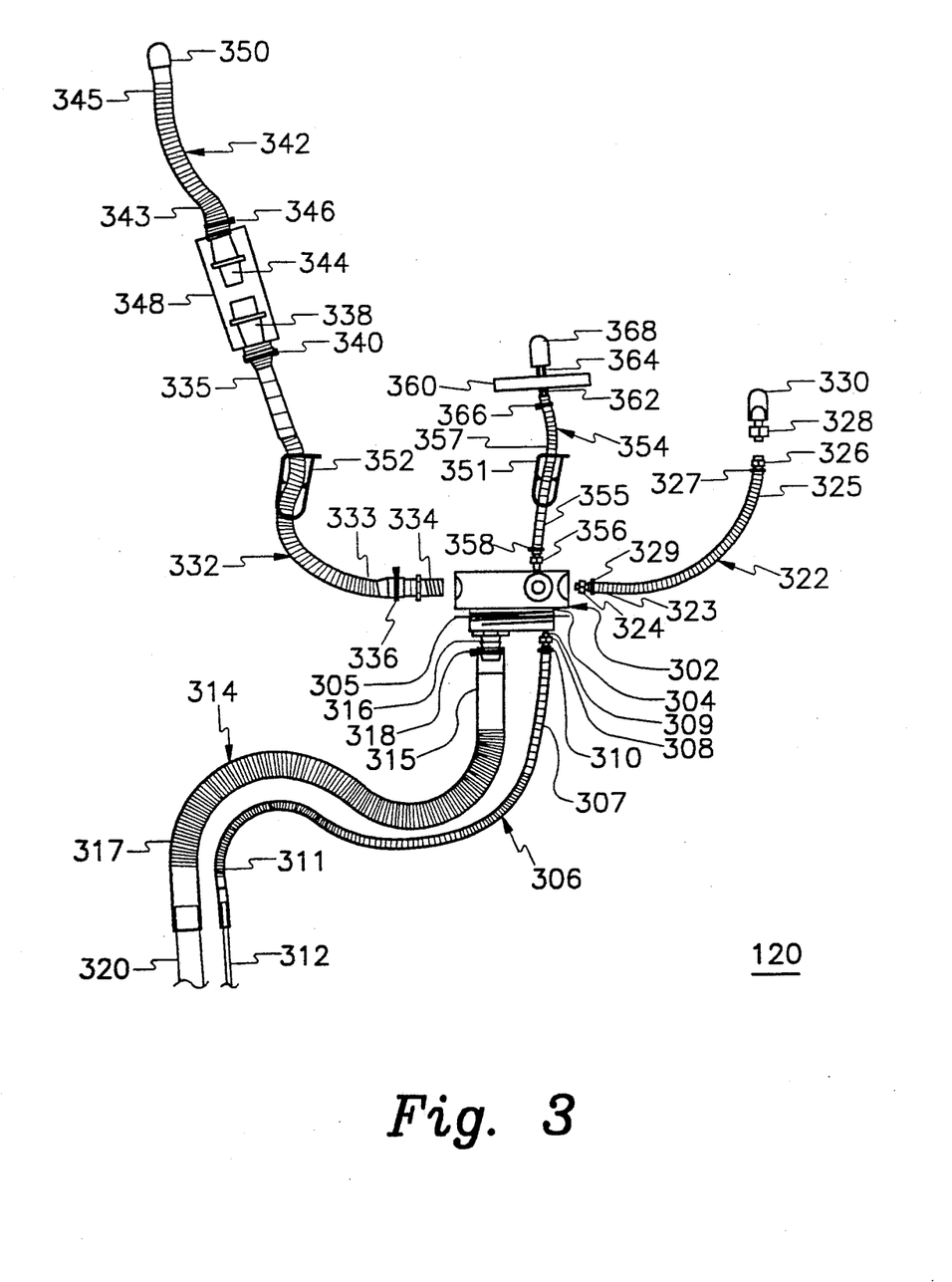
FIG. 3 is a detailed view of the dispensing assembly.

As shown in FIG. 3, dispensing assembly 120 first comprises a dispensing cap 302. As will be more fully discussed herein, dispensing cap 302 is custom designed to have several ports (shown in FIG. 6) which provide various functions and features. In the preferred embodiment, these ports are for dispensing high volumes of liquid media, sampling small volumes of liquid media, and for venting the internal compartment of the drum 110.

Dispensing cap 302 of the preferred embodiment is also made from high density polyethelene. High density polyethelene is the preferred material because it is compatible with the gamma irradiation process.

Dispensing cap 302 is designed to attach via buttress threads 304 to dispensing port 210 of drum 110. Dispensing cap 302 further comprises a gasket 305. Gasket 305 is provided so that dispensing cap 302, when fastened, will be in sealable contact with dispensing port 210 of drum 110. Gasket 305 is of conventional design and readily available from a variety of manufacturers. Gasket 205 should likewise be suitably compatible with the radiation processes.

Dispensing assembly 120 further comprises an internal sampling line 306. Internal sampling line 306 has a first end 307 and a second end 311. Internal sampling line 306 is provided to carry liquid from the bottom of drum 110 through the dispensing cap 302 and to an external sampling line 322 (to be described).

Sampling line 306 of the preferred embodiment is made from flexible ¼ inch tubing. It should be readily apparent, however, that sampling line 306 can be made in a variety of sizes and from a variety of materials. Choice of size may depend on the quantity of material to be sampled and the sampling device to be used.

Sampling line 306 of the preferred embodiment is made from a material compatible with the radiation processes and in particular the gamma irradiation process. In the preferred embodiment, internal sampling line 306 is made of a thermoplastic elastomer (C-FLEX®) available from Concept Polymer Technologies, Inc., Clearwater, Fla.

Figure 6:
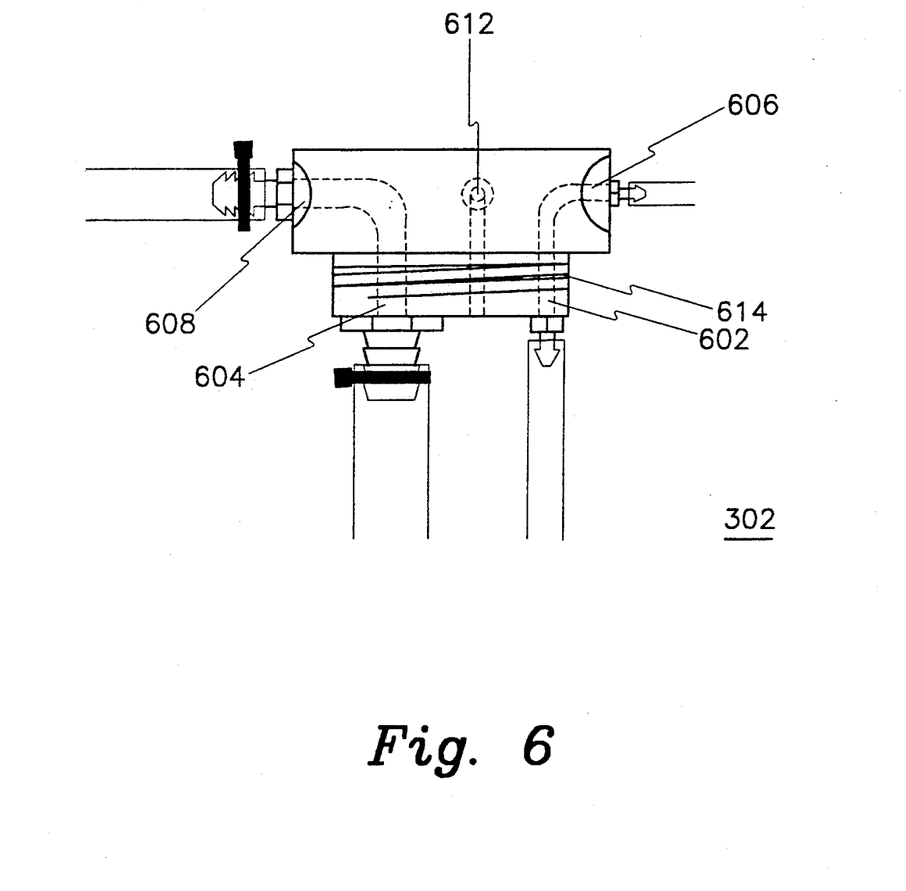
FIG. 6 is a detailed view of the dispensing cap.

Internal sampling line 306 is connected to an internal sampling port 602 (to be described) of dispensing cap 302 via a barbed bulkhead fitting 308. Bulkhead fitting 308 is formed with threads 309 that screwably connect with corresponding threads in the internal sampling port (not shown) of dispensing cap 302. To ensure that internal sampling line 306 is securely fastened to bulkhead fitting 308, a tie wrap is attached around internal sampling line 306.

Bulkhead fitting 308 is of conventional barbed design. As should be readily apparent, however bulkhead fitting 308 may be chosen from a variety of interconnect configurations.

Bulkhead fitting 308 of the preferred embodiment is also made from high density polyethelene. High density polyethelene is the preferred material because it is compatible with the gamma irradiation process.

Internal sampling line 306 further has attached a glass rod 312. Glass rod 312 is frictionally fit into the second end 311 of sampling line 306. Glass rod 312 is provided to thereby maintain the position of sampling line 306 at the bottom of drum 110. Because internal sampling line 306 is made of a plastic material, internal sampling line 306 may tend to float within the liquid.

Glass rod 312 is of conventional design and made from standard Type III borosilicate. Type III borosilicate is compatible with the gamma irradiation process. Glass rod 312, however, may be made from materials other than glass, such as metal. Care must be taken to ensure that the chosen material will not contaminate the liquid and that it is compatible with the gamma irradiation sterilizing process.

Dispensing assembly 120 further comprises an internal dispensing line 314. Internal dispensing 314 has a first end 315 and a second end 317. First end 315 of internal dispensing line 314 is connected to the barbed end of a bulkhead fitting 316. Bulkhead fitting 316 is securely attached to an internal dispensing port 604 (to be described) of dispensing cap 302. Internal dispensing line 314 is provided to carry high volumes of liquid from drum 110. Internal dispensing line 314 is securely attached to the barbed end of bulkhead fitting 316 using a tie wrap 318.

Internal dispensing line 314 of the preferred embodiment is also made from a material compatible with the radiation processes and in particular the gamma irradiation process. In the preferred embodiment, sampling line 306 is made of a thermoplastic elastomer (C-FLEX ®) available from Concept Polymer Technologies, Inc., Clearwater, Fla.

Bulkhead fitting 316 of the preferred embodiment is also made from high density polyethelene. High density polyethelene is the preferred material because it is compatible with the gamma irradiation process.

Dispensing assembly 120 further comprises a glass rod 320. Glass rod 320 is frictionally fitted to the second end 317 of internal dispensing line 314. Glass rod 320, like glass rod 312, is provided to ensure that internal dispensing line 314 remains positioned substantially at the bottom of drum 110. Glass rod 320 is of the same design and material as is glass rod 312.

As can be seen from the above discussion, internal sampling line 306 and internal dispensing line 314 are positioned within drum 110. Internal sampling line 306 and internal dispensing line 314 of the preferred embodiment are of the same length and the same type of flexible tubing. In addition, internal sampling line 306 and internal dispensing line 314 are designed to have a length such that the lower end of glass rods 312 and 320 will be substantially at the bottom of drum 110. Moreover, internal sampling line 306, external dispensing line 314, and glass rods 312 and 320 are designed such as to be compatible with the gamma irradiation sterilizing process.

As also shown in FIG. 3, dispensing assembly 120 further comprises an external sampling line 322. First end 323 of external sampling line 322 has a first end 323 and a second end 325. First end 323 of external sampling line 322 is connected to dispensing cap 302 via a bulkhead fitting 324. External sampling line 322 is connected to the barbed end of bulkhead fitting 324 and securely fastened thereto using a tie wrap 325.

External sampling line 322 of the preferred embodiment is made from a material compatible with the radiation processes and in particular the gamma irradiation process. In the preferred embodiment, external sampling line 322 is made of a thermoplastic elastomer (C-FLEX ®) available from Concept Polymer Technologies, Inc., Clearwater, Fla.

Bulkhead fitting 324 of the preferred embodiment is made from high density polyethelene. High density polyethelene is the preferred material because it is compatible with the gamma irradiation process.

As also shown in FIG. 3, further attached to the second end 325 of sampling line 322 is a male luer adapter 326. Male luer adapter 326 is attached to the second end 325 of external sampling line 322 via a tie wrap 327. As will be shown herein, male luer adapter 326 is provided so that the user may have an optional method of sampling the liquid. As will also be discussed, it is possible for the user to supplement liquid media via male luer adaptor 326.

Male luer adapter 326 is of conventional design and can be readily purchased from a variety of manufacturers. Male luer adaptor 326 of the preferred embodiment is made from high density polyethelene.

Also shown attached to male luer adapter 326 is a septum 328. Septum 328 is removably connected to male luer adaptor 326. Septum 328 is of conventional injection port design and is provided so that sampling of the liquid media contained in drum 110 may be performed using a syringe or the like. Septum 328 is available from a variety of medical supply houses. Septum 328 of the preferred embodiment has a rubber septum and a polycarbonate housing.

A cap 330 is provided on septum 328 so that septum 328 will not become contaminated. Cap 330 of the preferred embodiment is made from polyvinyl chloride (PVC)

As also shown by FIG. 3, dispensing assembly 120 further comprises an external dispensing line 332. External dispensing line 332 provides the primary method of dispensing high volumes of liquid from the drum 110. External dispensing line 332 has a first end 333 and a second end 335. The first end 333 of external dispensing line 332 is connected to dispensing cap 302 via a bulkhead fitting 334. First end 333 of external sampling line 332 is securely fastened to the barbed end of bulkhead fitting 334 using a tie wrap 336.

Attached to the second end 335 of external dispensing line 332 is a female connector 338. Female connector 338 is provided so that the user may connect the primary dispensing system. Connector 338 is securely fastened to the second end 335 of external dispensing line 332 using a tie wrap 340.

External sampling line 322 is a material compatible with the radiation processes and in particular the gamma irradiation process. In the preferred embodiment, sampling line 306 is made of a thermoplastic elastomer (C-FLEX ®) available from Concept Polymer Technologies, Inc., Clearwater, Fla.

Bulkhead fitting 334 of the preferred embodiment are made from high density polyethelene.

Female connector 338 is of conventional interconnect design. Female connector 338, however, may embody other interconnect configurations as long as it is compatible with the mating connector to be used by the end user. Female connector 338 of the preferred embodiment is likewise made from high density polyethelene. Like several other components of the present invention previously discussed, high density polyethelene is chosen because it is compatible with gamma irradiation sterilization protocols.

Further shown is an auxiliary external dispensing line 342. Auxiliary external dispensing line 342 is generally provided to allow the user to fill the drum 110. Auxiliary external dispensing line 342 has a first end 343 and a second end 345. Auxiliary external dispensing line 342 has attached at the first end 343 a male connector 344. Male connector 344 is secured to first end 343 of auxiliary external dispensing line 342 using a tie wrap 346.

Male connector 344 of auxiliary external dispensing line 342 is removably connected with female connector 338 of external dispensing line 332. However, the female connector 338 and male connector 344 assembly is enclosed by heat-shrinkable wrap 348. Heat-shrinkable wrap 348 can be removed by the user such that male connector 344 and female connector 338 may be engaged and disengaged as required by the user. A flow clamp 352 is shown attached to external dispensing line 332. Flow clamp 352 is generally provided so that the flow of fluid through external dispensing line 332 can be stopped by a user. Flow clamp 352 operates by pinching external dispensing line 332.

Attached to the second end 345 of auxiliary external dispensing line 342 is a protective cap 350. Protective cap 350 ensures that no contaminants enter auxiliary external dispensing line 342.

When filling is desired, the end user removes the protective cap 350 and suitably fills the drum 110 with liquid media. After filling is complete, auxiliary external dispensing line 342 is closed off. Thereafter, auxiliary dispensing line 342 remains connected to the dispensing assembly 120 as a protective device only.

Auxiliary external dispensing line 342 and Protective cap 350 of the preferred embodiment are made from polyvinyl chloride (PVC).

Male connector 344 is made from high density polyethelene.

As also shown by FIG. 3, dispensing assembly 120 further comprises a venting line 354. Venting line 354 is provided so that the pressure within drum 110 will always remain at atmospheric conditions. Venting line 354 has a first end 355 and a second end 357. Venting line 354 is connected to dispensing port 302 via a bulkhead fitting 356. First end 355 of vent line 354 is securably attached to the barbed end of bulkhead fitting 356 using a tie wrap 358.

Venting line 354 of the preferred embodiment is made from a material compatible with the radiation processes and in particular the gamma irradiation process. In the preferred embodiment, sampling line 306 is made of a thermoplastic elastomer (C-FLEX ®) available from Concept Polymer Technologies, Inc., Clearwater, Fla.

Bulkhead fitting 356 of the preferred embodiment is made from high density polyethelene. Like several other components of the present invention previously discussed, high density polyethelene is chosen because it is compatible with gamma irradiation sterilization protocols.

As also shown in FIG. 3, attached to the second end 357 of vent line 354 is an air filter 360. Air filter 360 is provided to ensure that no contaminants enter drum 110 via vent line 354. Air filter 360 is also used to maintain sterility of air venting in and out of the drum 110.

Air filter 360 is of conventional design and in the preferred embodiment has a porosity of approximately 0.20 microns. Air filter 360 is a two-way hydrophobic filter and should be kept dry for optimum performance. Air filter 360 is made from polypropelene or polycarbonate. The filter membrane is made of radiation compatible material. The air filter 360 is available from Millipore Corp., Bedford, Mass. or Gelman Sciences, Inc., Ann Arbor, Mich. Like the other components of the present invention previously discussed, high density polyethelene is chosen because it is compatible with gamma irirradiation sterilization protocols.

Air filter 360 has a barbed end 364 which is adapted to receive a protective cap 368. Protective cap 368 is provided so that no contaminants may unnecessarily enter air filter 360.

Air filter 360 further has a barb fitting 362. Barb fitting 362 is provided so as to receive one end of vent line 354. Vent line 354 is securably attached to barb fitting 362 of air filter 360 using a tie wrap 366. A flow clamp 351 is shown attached to vent line 354.

Figure 4:
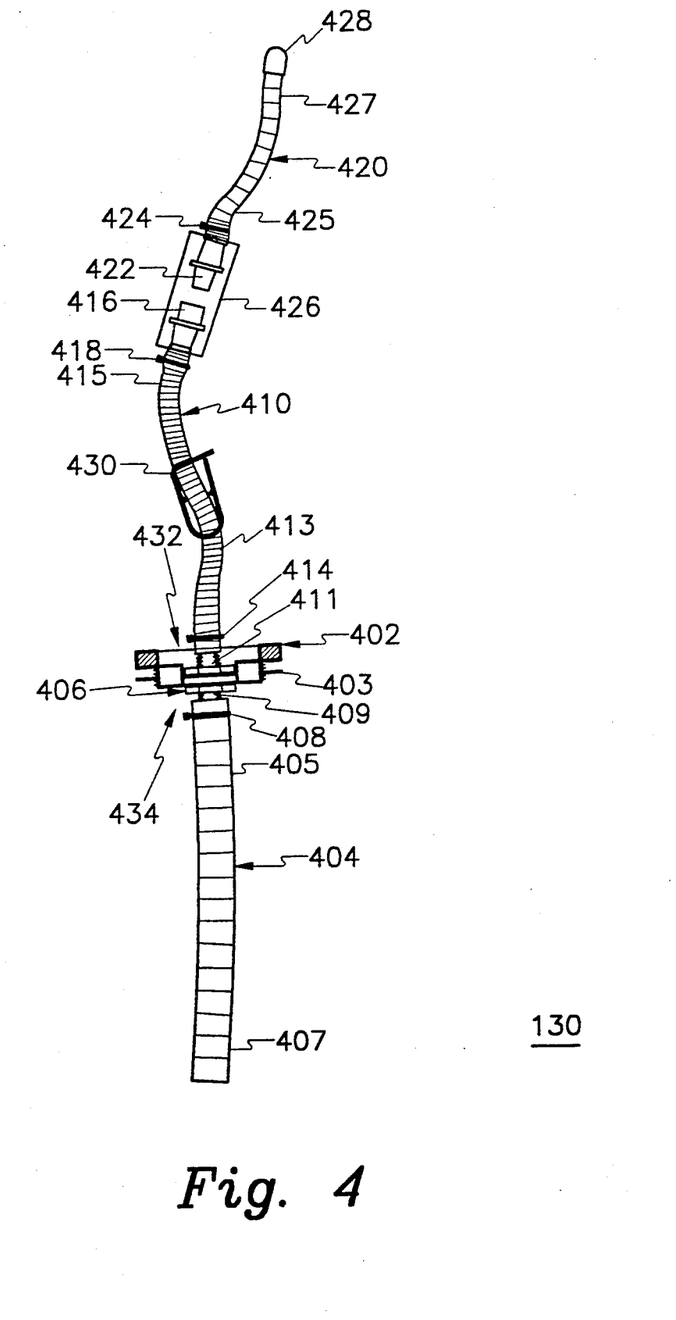
FIG. 4 is a detailed view of the supplementation assembly.

As shown in FIG. 4, supplementation assembly 130 generally first comprises a supplementation cap 402. Supplementation cap 402 securely mounts into supplementation port 215 of drum 110.

Supplementation cap 402 is of conventional design and can be purchased from the Rieke Corporation. Supplementation cap 402 of the preferred embodiment is made from high density polyethelene. Like several other components of the present previously discussed, high density polyethelene is chosen because it is compatible with gamma irirradiation sterilization protocols.

Supplementation cap 402 has an inlet port 432 and an outlet port 434 which are in communication with each other. Also provided is a gasket 403 which ensures good sealed contact between supplementation cap 402 and supplementation port 210 of drum 110.

Supplementation assembly 130 further comprises an internal supplementation line 404. Internal supplementation line 404 is generally provided to supplement (add) various liquids to the liquid of drum 110 as desired by the end user. Internal supplementation line 404 has a first end 405 and a second end 407. The first end 405 of internal supplementation line 404 is attached to supplementation cap 402 using a bulkhead fitting 406. Bulkhead fitting 406 of the preferred embodiment is of a one-piece design and, as shown in FIG. 4, has two ends 409 and 411. Ends 409 and 411 are barbed. Inlet port 432 is formed through end 411 of bulkhead fitting 406. Outlet port 434 is formed through end 409 of bulkhead fitting 406.

Internal supplementation line 404 in the preferred embodiment is made from a material compatible with the radiation processes and in particular the gamma irradiation process. In the preferred embodiment, sampling line 306 is made of a thermoplastic elastomer (C-FLEX ®) available from Concept Polymer Technologies, Inc., Clearwater, Fla.

Bulkhead fitting 406 of the preferred embodiment is made from high density polyethelene.

As shown, the first end 405 of internal supplementation line 404 is attached to barbed end 409 of bulkhead fitting 406 using a tie wrap 408.

Supplementation assembly 130 further comprises an external supplementation line 410. External supplementation line 410 has a first end 413 and a second end 415. Like internal supplement line 404, first end 413 of external line 410 is attached to the barbed end 411 of bulkhead fitting 406 using a tie wrap 414.

External supplementation line 410 of the preferred embodiment is made from a material compatible with the radiation processes and in particular the gamma irradiation process. In the preferred embodiment, sampling line 306 is made of a thermoplastic elastomer (C-FLEX ®) available from Concept Polymer Technologies, Inc., Clearwater, Fla.

The second end 415 of external supplementation line 410 is attached to a male connector 416. The second end 415 of external supplementation line 410 is secured to male connector 416 using a tie wrap 418. Male connector 416 provides an interconnect area for the user to connect to so that they may supplement the liquid in the drum 110. Male connector 416 of the preferred embodiment is made from high density polyethelene.

As also shown by FIG. 4, supplementation assembly 130 further comprises an auxiliary external supplementation line 420. Auxiliary external supplementation line 420 has a first end 425 and a second end 427. First end 425 of auxiliary external supplementation line 420 is connected to a female connector 422 and secured using a tie wrap 424. Female connector 422 is removably connected with male connector 416.

Auxiliary external supplementation line 420 of the preferred embodiment is made from PVC material.

Female connector 442 of the preferred embodiment is made from high density polyethelene.

The female connector 422 and male connector 416 assembly is enclosed by heat-shrinkable wrap 426. Heat-shrinkable wrap 426 can be removed by the end user so that female connector 422 and male connector 416 can be disengaged, thereby allowing the end user access to supplement drum 110 via male connector 416.

As also shown by FIG. 4, the second end 427 of auxiliary external supplementation line 420 has connected thereto a protective cap 428. Protective cap 428 ensures that no contaminants from the environment enter the auxiliary external supplementation line 420 and thus drum 110.

Protective cap 428 of the preferred embodiment is made from high density polyethelene. Like other components of the present invention, high density polyethelene is chosen because it is compatible with gamma irirradiation sterilization protocols.

Further shown in FIG. 4 is a flow clamp 430. Flow clamp 430 is shown attached to external supplementation line 410. Flow clamp 430 is generally provided so that the flow of fluid can be stopped. Flow clamp 430 in operation pinches or shuts off external supplementation line 410. Flow clamp 430 should be clamped whenever supplementation assembly 130 is not in operation.

Heretofore, the present invention has been discussed in terms of either aseptically dispensing or aseptically supplementing. FIG. 3 shows an embodiment wherein the sterile liquid media within drum 110 can be aseptically dispensed via dispensing line 332 or via sampling line 322. FIG. 4, as discussed, shows supplementation assembly 130 which allows the user to aseptically supplement the sterile liquid media within drum 110.

Another significant feature of the present invention is that of aseptically mixing the secondary sterile liquid with the primary sterile liquid. In other words, after supplementation, the user may mix the supplement liquid and the liquid originally contained in drum 110. Mixing of the supplement liquid with the original liquid is necessary so that a uniform composition can be achieved.

Figure 5:
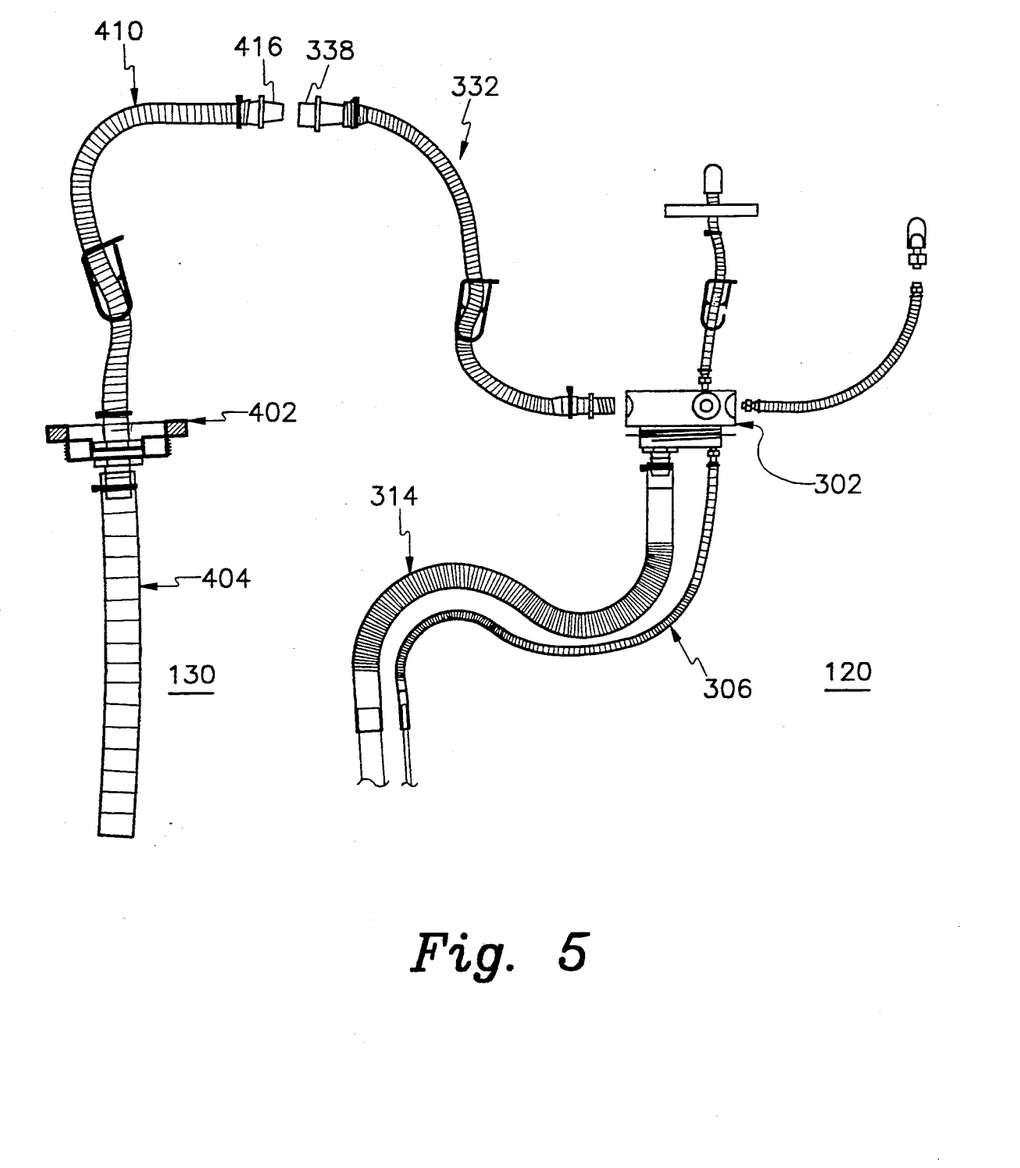
FIG. 5 is shows the mixing embodiment of the present invention.

Referring now to FIG. 5, the aseptic mixing embodiment of the present invention is illustrated in more detail. As shown by FIG. 5, connector 416 has been disengaged from connector 422 of auxiliary supplementation line 420. Likewise, connector 338 of external dispensing line 332 has been disengaged from connector 344 of auxiliary dispensing line 342.

In the mixing embodiment, the user may connect male connector 416 with female connector 338. Upon engagement of male connector 416 and female connector 338, a communication loop between the bottom of drum 110 and the top of drum 110 is established. As can readily be seen, upon application of an external pumping action (not shown), the liquids contained within drum 110 will be caused to circulate from the bottom of the drum 110 to the top of the tank. This circulation action ensures that the supplemented liquid is fully mixed with the original liquid contained within drum 110. The mixing feature is aseptic because each of the components that comes in contact with the sterile liquid is irradiated with gamma irradiation to thereby become sterilized.

As shown in FIG. 6, dispensing cap 302 comprises an internal sampling port 602, an internal dispensing port 604, an external sampling port 606, an external dispensing port 608, and a venting port 612.

Internal sampling port 602 is in communication with external sampling portion 606 to thereby provide access from the inside of drum 110 to the external environment. As discussed before, internal bulkhead fitting 309 connects to internal supply port 602, while bulkhead fitting 324 connects to external sampling port 606.

Dispensing cap 302 has also formed buttress threads 614. Buttress threads 602 are designed such as to mate with the corresponding buttress threads on the dispensing port 210 of drum 110.

As previously discussed, each of the components that come into contact with the sterile liquid(s) are pre-sterilized with sterilization process. One sterilization process in the preferred embodiment of the present invention is that of the gamma irradiation sterilization process. The materials should be chosen such that they will be chemically compatible with such a process. This is important in order to maintain an aseptic supplementation, mixing and dispensing system. In particular, it should be emphasized that components that are continuously exposed to the sterile liquids should be very compatible with the sterilization process in order to ensure a sterile system. Components which have less contact with the sterile fluid may be less compatible.

The following will be a discussion of the preferred operation of the present invention. When aseptically filling the system of the present invention, protective cap 350 is removed. Thereafter, an external filling bell (not shown) is attached to second end 345 of auxiliary external dispensing line 342 to thereby insert the liquid to be filled. The sterile liquid to be filled passes through the male connector 344/female connector 338 connection, down through external dispensing line 332, through dispensing cap 302, down internal dispensing line 314 and into drum 110.

Thereafter, the external dispensing line 332 is pinched or closed such that no other liquid can be added via auxiliary external dispensing line 342. Thereafter, the end user may either directly aseptically dispense the liquid that was filled into drum 110 or they may aseptically supplement with a second liquid.

If direct dispensing is desired, the and user will remove heat shrinkable wrap 348 and disengage male connector 344 from female connector 338. Thereafter, female connector 340 can be connected by the end user to an appropriate external device such as a reaction vessel.

If the user, however, desires to supplement the liquid contained in drum 110, they will remove heat shrinkable wrap 426 from supplementation assembly 130. Thereafter, the end user will disengage female connector 422 from male connector 416. This disengagement allows the end user to connect an appropriate supplementing means (not shown) to female connector 416. The supplemented liquid flows through female connector 416, down external supplementation line 410, through supplementation cap 402 and down internal supplementation line 404 into drum 110.

At this point, the original sterile fluid in drum 110 has been supplemented with a second sterile fluid. Thereafter, the end user may either dispense the first and second fluid as pending and as previously discussed in the prior dispensing discussion, or they may initiate the aseptic mixing mode of the present invention.

In the aseptic mixing operation, the end user connects female connector 338 of dispensing assembly 120 to male connector 416 of the supplementation assembly 130. Upon application of an external pumping action by a suitable pumping apparatus (not shown), the liquid at the bottom of tank 110 is caused to be recirculated to the top of tank 110. Finally, it should also be noted that whenever the system of the present invention is not in operation, flow clamps 430 and 352 should be tightened to maintain fluid within drum 110.

The foregoing description is intended primarily for purposes of illustration. The present invention may be embodied in other forms or carried out in other ways without departing from the spirit and scope of the invention. Modifications and variations still falling within the spirit and scope of the present invention will be readily obvious to those skilled in the art.

What is claimed is:

1. An apparatus for dispensing and supplementing a first sterile liquid with a second sterile liquid, the apparatus comprises:
   (a) a drum having a first bunge opening and a second bunge opening;
   (b) a first member mounted with said first bunge opening and configured to allow the filling of said drum with the first sterile liquid;
   (c) a second member mounted with said second bunge opening and configured to allow the filling of said drum with the second sterile liquid and to thereby supplement the first sterile liquid with the second sterile liquid;
   (d) said first member being further configured to allow for the dispensing of the first sterile liquid and the second sterile liquid; and
   (e) said drum, said first member, and said second member being made of a material compatible with a sterilization process to thereby maintain the sterility of the first sterile liquid and the second sterile liquid should said drum, said first member or said second member come in contact with the first sterile liquid and the second sterile liquid.

2. The apparatus of claim 1, wherein said first member comprises a filling and dispensing line configured to allow the filling of said drum with the first sterile liquid and the dispensing of the first sterile liquid and the second sterile liquid from said drum.

3. The apparatus of claim 2, wherein said first member further comprises a sampling line configured to allow the sampling of the first liquid and the second sterile liquid contained in said drum.

4. The apparatus of claim 3, wherein said second member comprises a supplementation line configured to allow the filling of said drum with the second sterile liquid.

5. The apparatus of claim 4, wherein said material is a thermoplastic elastomer.

6. An apparatus for dispensing and supplementing a first sterile liquid with a second sterile liquid, the apparatus comprises:
   (a) a drum;
   (b) a first member mounted with said drum and configured to allow the filling of said drum with the first sterile liquid;
   (c) a second member mounted with said drum and configured to supplement the first sterile liquid with the second sterile liquid;
   (d) said first member being further configured to allow for the dispensing of the first sterile liquid and the second sterile liquid;
   (e) said first member being further configured to connect with said second member such that the first sterile liquid can be mixed with the second sterile liquid; and
   (e) said drum, said first member, and said second member being made of a material compatible with a sterilization process to thereby maintain the sterility of the first sterile liquid and the second sterile liquid should said drum, said first member or said second member come in contact with the first sterile liquid and the second sterile liquid.

7. The apparatus of claim 6, wherein said first member comprises a filling and dispensing line configured to allow the filling of said drum with the first sterile liquid and the dispensing of the first sterile liquid and the second sterile liquid from said drum.

8. The apparatus of claim 7, wherein said first member further comprises a sampling line configured to allow the sampling of the first liquid and the second sterile liquid contained in said drum.

9. The apparatus of claim 8, wherein said second member comprises a supplementation line configured to allow the filling of said drum with the second sterile liquid.

10. The apparatus of claim 9, wherein said filling and dispensing line can be connected with said supplementation line to form a mixing loop, whereby the first sterile liquid and the second sterile liquid can be mixed upon application of an external pumping action.

11. The apparatus of claim 10, wherein said material is a thermoplastic elastomer.

* * * * *